United States Patent [19]

Davenport et al.

[11] Patent Number: 4,568,763

[45] Date of Patent: * Feb. 4, 1986

[54] PROCESS FOR PRODUCING N-ACYL-ACYLOXY AROMATIC AMINES

[75] Inventors: Kenneth G. Davenport; Charles B. Hilton, both of Corpus Christi, Tex.

[73] Assignee: Celanese Corporation, Corpus Christi, Tex.

[*] Notice: The portion of the term of this patent subsequent to Dec. 24, 2002, has been disclaimed.

[21] Appl. No.: 627,382

[22] Filed: Jul. 3, 1984

[51] Int. Cl.$^4$ ............... C07C 103/46; C07C 103/66; C07C 125/065; C07C 103/38

[52] U.S. Cl. ..................... 560/142; 260/404; 260/463; 560/9; 560/10; 560/24; 560/27; 560/28; 560/30; 560/33; 560/139; 560/141; 564/223

[58] Field of Search ............ 560/142, 108, 109, 139, 560/141; 564/223; 260/404, 463

[56] References Cited

U.S. PATENT DOCUMENTS 2,833,825  5/1978  Lewis ........................... 568/310
4,524,217  6/1985  Davenport et al. ............ 564/223

FOREIGN PATENT DOCUMENTS 2616986  10/1977  Fed. Rep. of Germany .

OTHER PUBLICATIONS

J. Pharmaceutical Sciences, vol. 59, No. 12, pp. 1738–1741; Rattie et al.

Fieser and Fieser, Organic Chemistry, 3rd Ed., Reinhold Publ. Corp., New York, 1956, pp. 211–212, 627.
Simons et al, J. Amer. Chem. Soc., 62, 485 and 486 (1940).
Dann and Mylius, Annalen der Chemie, 587 Band, 1–15, (W. Germany, 1954)–English translation provided.
Simons et al, J. Amer. Chem. Soc., 61, 1795 and 1796 (1939).
Auwers et al, Chemishe Berichte, 58, 36–51 (Germany 1925)–English translation provided.
Ganboa et al, Synthetic Communications, 13 (11) 941–944 (1983).
Pearson et al, J. Amer. Chem. Soc., 75, 5905–5908 (1953).

Primary Examiner—Natalie Trousof
Assistant Examiner—Patricia M. Scott
Attorney, Agent, or Firm—M. Turken; D. R. Cassady

[57] ABSTRACT

N-acyl-acyloxy aromatic amines, e.g. 4-acetoxyacetanilide (AAA), are prepared by reacting a hydroxy aromatic ketone, e.g. 4-hydroxyacetophenone, with hydroxylamine or a hydroxylamine salt and a base to obtain the ketoxime of the ketone, e.g. 4-hydroxyacetophenone oxime, and then subjecting the ketoxime to a Beckmann rearrangement and accompanying acylation by contacting the ketoxime with a carboxylic acid anhydride and a Beckmann rearrangement catalyst to form the N-acyl-acyloxy aromatic amine.

7 Claims, No Drawings

PROCESS FOR PRODUCING N-ACYL-ACYLOXY AROMATIC AMINES

This invention relates to the production of N-acylacyloxy aromatic amines, e.g. 4-acetoxyacetanilide (AAA) from hydroxy aromatic ketones, e.g. 4-hydroxyacetophenone.

BACKGROUND OF THE INVENTION

It is known to produce N-acyl-acyloxy aromatic amines, e.g. 4-acetoxyacetanilide, by preparing the sodium salt of the corresponding N-acyl-hydroxy aromatic amine, e.g. N-acetyl-para-aminophenol (APAP), and reacting the sodium salt with the appropriate carboxylic acid anhydride, e.g. acetic anhydride. The N-acyl-hydroxy aromatic amine, e.g. APAP, used as the starting material for the foregoing reaction is in turn prepared by acylating the corresponding hydroxy aromatic amine, e.g. para-aminophenol, with an acylating agent such as an anhydride, e.g. acetic anhydride. However the latter reaction may cause problems such as the difficulty of mono-acylating the hydroxy aromatic amine, oligomerization of the hydroxy aromatic amine, and color body formation.

The preparation of hydroxy aromatic ketones by the Fries rearrangment of aromatic esters is well-known in the art. Thus, Lewis, U.S. Pat. No. 2,833,825 shows the rearrangement of phenyl or other aromatic esters to acylphenols or other hydroxy aromatic ketones using anhydrous hydrogen fluoride as catalyst. The examples of this patent are limited to the rearrangement of esters of higher fatty acids with the yields ranging from 55 to 95%.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15 (1954), show the rearrangement of phenyl acetate in hydrogen fluoride to 4-hydroxyacetophenone, with a maximum yield of 81% after 24 hours of reaction time, and report a yield of 92% stated to be obtained by K. Weichert as reported in Angewandte Chemie 56, 338 (1943). However, Dann and Mylius suggest that the difference in yields may be at least partly due to the previous ignoring by Weichert of the accompanying 2-hydroxyacetophenone.

Dann and Mylius also disclose the reaction of phenol and glacial acetic acid in the presence of hydrogen fluoride to produce 4-hydroxyacetophenone at a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone in 40% yield.

Meussdoerffer et al, German Offenlegungsschrift 26 16 986 published Oct. 27, 1977 and assigned to Bayer AG, disclose the acylation of phenolic compounds such as phenol itself with an acyl halide such as acetyl chloride to form hydroxy aromatic ketones.

Auwers et al, Chemische Berichte 1925, 58, 36–51, at page 41 show the Beckmann rearrangement of a large number of oximes of aromatic ketones most of which are substituted acetophenones. However, the only attempted rearrangement of the oxime of a ring-unsubstituted hydroxy aromatic ketone was that of the oxime of o-hydroxyacetophenone, but no amine was formed, i.e. the attempted rearrangement was unsuccessful; see Auwers et al at page 41.

Ganboa et al, Synthetic Communications 13(11), 941–944 (1983) show the production of acetanilide from acetophenone by refluxing in a solution of hydroxylamine hydrochloride. There is however no suggestion of the synthesis of N-acylacyloxy aromatic amines such as 4-acetoxyacetanilide (AAA).

Pearson et al, Journal of the American Chemical Society 75 5905–5908 (Dec. 5, 1953) disclose the formation of hydrazones from ketones by reaction with hydrazine hydrate and the rearrangement of the hydrazone to the amide by reaction with sodium nitrite and concentrated sulfuric acid. Specifically, on page 5907 Pearson et al show the rearrangement of p-hydroxyacetophenone hydrazone to p-hydroxyacetanilide, i.e. APAP.

SUMMARY OF THE INVENTION

In accordance with one aspect of this invention, N-acyl-acyloxy aromatic amines, e.g. 4-acetoxyacetanilide (AAA), are produced by reacting a hydroxy aromatic ketone, e.g. 4-hydroxyacetophenone (4-HAP), with hydroxylamine or a hydroxylamine salt, to form the ketoxime of the ketone and subjecting the ketoxime to a Beckmann rearrangement and accompanying acylation by contacting the ketoxime with a carboxylic acid anhydride and a Beckmann rearrangement catalyst to form the N-acyl-acyloxy aromatic amine.

The ketoxime formation of this invention proceeds as indicated in equation (I):

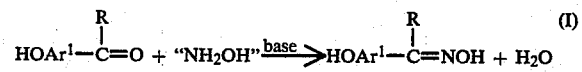

When AAA is the desired product the ketoxime formation proceeds as in equation (II):

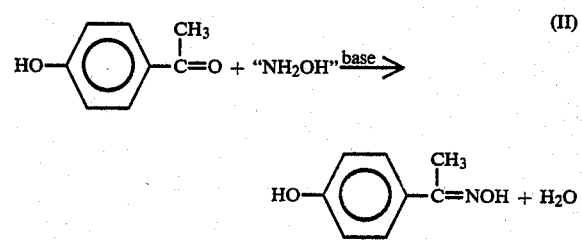

The Beckmann rearrangement and accompanying acylation of this invention proceeds as in equation (III):

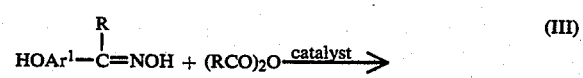

-continued

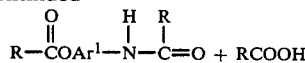

while the Beckmann rearrangement and accompanying acetylation when AAA is the desired product proceeds as in equation (IV):

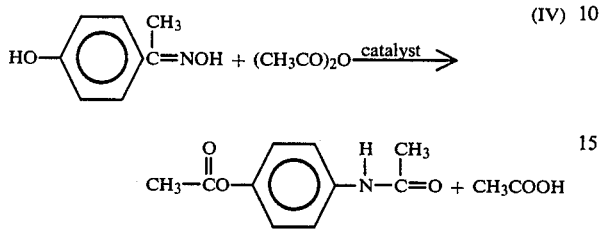

In equations I and III, $Ar^1$ is a divalent aromatic radical. The specific nature of the radical is not critical but it is preferably a radical resulting from the removal of two ring hydrogen atoms from benzene, naphthalene, or biphenyl, either unsubstituted or with ring hydrogens substituted with radicals such as alkyl, alkenyl, alkynyl, alkoxy or acyloxy containing 1 to 18 carbon atoms, aralkyl containing 7 to 18 carbon atoms; halogen, e.g. chlorine, bromine, or iodine; hydroxy; amino; or sulfhydryl. $Ar^1$ is preferably 1,4-phenylene, 2,1-naphthylene, 2,6-naphthylene, 5-phenyl-1,2-phenylene, 3-phenyl-1,4-phenylene or 3-methyl-1,4-phenylene with the ketocarbon and corresponding groups occupying the first stated numbered position of $Ar^1$ when the positions are not equivalent. Most preferably $Ar^1$ is 1,4-phenylene.

The R groups in the foregoing equations may be the same or different and are each a monovalent organic radical containing, for example 1 to 18 carbon atoms preferably 1 to 4 carbon atoms. R may be, for example, alkyl, alkenyl, alkynyl, alkoxy, acyl or acyloxy containing 1 to 18 carbon atoms, either unsubstituted or substituted with radicals such as halogen, e.g. chlorine, bromine, or iodine; hydroxy; amino; sulfhydryl; or an aryl radical, Ar which may be a monovalent radical corresponding to the definition of $Ar^1$ given above except that the carbon bonded to OH is bonded to a hydrogen instead. Preferably, R is the same in all occurrences in equations (I) and (III) and is methyl, ethyl, propyl, or n-butyl and most preferably methyl corresponding to the use of acetate esters and methyl ketones in the latter equations. The preferred specific hydroxy aromatic ketone used to form the oxime is 4-hydroxyacetophenone (4-HAP) and the preferred product is 4-acetoxyacetanilide (AAA).

The hydroxy aromatic ketone used to form the oxime may be prepared by any method known in the art. For example, it may be prepared by the Fries rearrangement of the corresponding aromatic ester as indicated by the following equation where Ar, $Ar^1$ and R have the definitions given above:

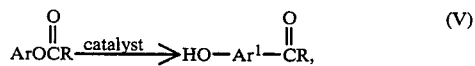

Alternatively, a phenolic compound and an acylating agent may be reacted in a Friedel-Crafts acylation to form the hydroxy aromatic ketone, in accordance with the following equation:

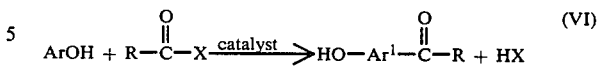

where Ar, $Ar^1$ and R have the meanings given previously and X is the residue minus the acyl group,

of the compounds which are known acylating agents, such as hydroxy, acyloxy, e.g. acetoxy, and halide, e.g. fluoride, chloride, bromide, and iodide. Examples of phenolic compounds which may be employed are phenol, 1-naphthol, 2-naphthol, 2-phenylphenol, 4-phenylphenol and o-cresol. Acylating agents which may be used are for example alkanoic acids, e.g. acetic and propionic acids, alkanoic acid anhydrides, e.g. acetic and propionic anhydrides, and acyl halides, e.g. acetyl and propionyl fluorides, chlorides, and bromides. Note that although the reaction of a phenolic compound and an acylating agent is characterized herein as a "Friedel-Crafts acylation," no opinion as to the mechanism of reaction should be implied by this characterization.

The catalyst for both of the foregoing reactions is preferably hydrogen fluoride but any other catalyst known in the art to be effective for the Fries and Friedel-Crafts reactions may be used, e.g. aluminum chloride, zinc chloride, or boron trifluoride.

In carrying out the reaction, the aromatic ester or phenolic compound and acylating agent, catalyst and if desired when an aromatic ester is the starting material, an additive for the reaction such as acetic anhydride or acetic acid, may be charged to a corrosion-resistant reactor and the mixture maintained at a temperature, for example, of about 20° to about 100° C. for a period, for example, of about ½ to about 4 hours, at a pressure, for example, of about 50 to about 500 psia. If HF is used as the catalyst it may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 75 moles per mole of aromatic ester or phenolic compound initially present in the reaction zone. If AAA is the desired product of the reaction, the starting material if a Fries rearrangement is employed will be phenyl acetate while phenol and an acetylating agent such as acetic acid is the starting material if a Friedel-Crafts acylation is utilized. In both cases, the starting material is converted to 4-HAP which is in turn converted by the process of this invention to AAA.

The conversion of hydroxy aromatic ketones, e.g. 4-HAP, into N-acyl-acyloxy aromatic amines, e.g. AAA, is accomplished by first forming the ketoxime from the hydroxy aromatic ketone as indicated by equations (I) and (II), by contacting the ketone with hydroxylamine or a hydroxylamine salt, e.g. hydroxylamine hydrochloride, hydroxylamine sulfate, hydroxylamine bisulfate, or hydroxylamine phosphate, and a base, e.g. ammonium hydroxide, potassium hydroxide, sodium hydroxide, or lithium hydroxide in an amount, for example, for 1 to 3 moles per mole of hydroxylamine, at a temperature, for example of 0° to 60° C. for a period, for example, of 1 to 4 hours. Any pressure may be used, e.g. 80 mm. of mercury to 10 atmospheres absolute. The reaction is preferably carried out in an aqueous or alcoholic medium, i.e. in the presence of water and/or an alcohol such as methanol, ethanol, or isopropanol.

The ketoxime is converted into the corresponding N-acyl-acyloxy aromatic amine by a Beckmann rearrangement and accompanying acylation as shown in equations (III) and (IV), by contacting the ketoxime with the appropriate carboxylic acid anhydride and a Beckmann rearrangement catalyst at a temperature, for example of 0° to 118° C. for a period for example of 1 to 4 hours. As defined in the foregoing equations, any of a broad class of anhydrides may be used but the anhydride is preferably that of an alkanoic acid containing 2 to 4 carbon atoms, e.g. acetic anhydride, propionic anhydride, or n-butyric anhydride. The pressure is not critical and may be, for example, in the range of 80 mm. of mercury to 10 atmospheres absolute. Any Beckmann rearrangement catalyst may be used, as for example, an acid, e.g. a mineral acid such as sulfuric or hydrochloric acid, an organic acid such as trifluoroacetic acid, para-toluenesulfonic acid, benzenesulfonic acid or methanesulfonic acid, a sulfonic acid ion-exchange resin such as Amberlyst 15 or Nafion 501, or thionyl chloride in liquid sulfur dioxide. The reaction may be advantageously carried out in the presence of the glacial carboxylic acid corresponding to the anhydride employed in the reaction in an amount, for example up to 50% by weight of the anhydride. The total amount of glacial carboxylic acid is not critical but the total amount of anhydride or anhydride/acid mixture is such that the ketoxime concentration is in most cases in the range of about 2 to 50% by weight at the start of the reaction.

The following examples further illustrate the invention.

EXAMPLE 1

This example illustrates the preparation of 4-hydroxyacetophenone by the Fries rearrangement of phenyl acetate using hydrogen fluoride as catalyst.

To a 300 cc Hastelloy C autoclave was charged 40.8 g (0.3 mol) of phenyl acetate. The autoclave was sealed, immersed in a dry ice/isopropanol bath and cooled internally to −45° C., and evacuated to ca. 100 Torr. Addition of 120 g (6.0 mol) of anhydrous hydrogen fluoride was performed in a manner such as that the internal temperature of the autoclave did not exceed 0° C. The internal pressure of the reactor was then adjusted to 0 psig with nitrogen. The contents of the autoclave were stirred and heated to 75° C. for 1 h. The hydrogen fluoride was vented over a 45 min period at ca. 45° C. The mixture was poured onto 25 g of ice and neutralized with 45% potassium hydroxide solution. The aqueous mixture was extracted with ethyl acetate. The organic fraction was then dried over anhydrous magnesium sulfate, filtered, and the solvent was removed on a rotary evaporator to yield 44.0 g of a dark green solid corresponding to 99.9% conversion of phenyl acetate and 94.3% selectivity to 4-hydroxyacetophenone.

EXAMPLE 2

This example illustrates the preparation of 4-hydroxyacetophenone by the Fries rearrangement of phenyl acetate using hydrogen fluoride as catalyst with acetic anhydride as additive.

To a 300 cc Hastelloy C autoclave were added 30.6 grams (0.3 mole) of acetic anhydride. The autoclave was cooled to −50° C. and evacuated to 5 Torr whereupon 120 g (6.0 mole) of anhydrous hydrogen fluoride was transferred from a cylinder to the autoclave. After the transfer of hydrogen fluoride was completed, the internal temperature and the internal pressure of the autoclave was adjusted to −50° C. and 0 psig using nitrogen, respectively. To the stirred autoclave was added 81.6 g (0.6 mol) of phenyl acetate at such a rate that the temperature of the mixture did not exceed −23° C. Upon completion of phenyl acetate addition, the contents were warmed to 50° C. and stirred for 3 h during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using 45% potassium hydroxide and the mixture was then extracted with 75 ml of ethyl acetate (3×). The organic solution was dried over anhydrous magnesium sulfate, filtered, and the solvent was removed using a rotary evaporator.

The reaction proceeded with 98.1% conversion of phenyl acetate and with the following selectivities: phenol 1%; 4-hydroxyacetophenone (4-HAP) 82.3%; 2-hydroxyacetophenone (2-HAP) 4.3%; 3-hydroxyacetophenone (3-HAP) 0.1%; 4-acetoxyacetophenone (4-AAP) 3.8%; and 4-(4'-hydroxyphenyl)-acetophenone (HPAP) 0.4%.

EXAMPLE 3

This example describes the formation of 4-hydroxyacetophenone by the Fries rearrangement of phenyl acetate using hydrogen fluoride as catalyst and acetic acid as additive.

The procedure for Example 2 was repeated except that 18 grams (0.3 mole) of acetic acid rather than acetic anhydride were charged to the reactor before it was cooled and charged with the hydrogen fluoride. A conversion of 99.0% of phenyl acetate was obtained with the following selectivities: phenol 3.3%; acetic acid 0.8%; 4-HAP 80.8%; 3-HAP-0; 2-HAP 5.8%; 4-AAP 0.3%; and HPAP 0.3%.

EXAMPLE 4

This example illustrates the preparation of 4-hydroxyacetophenone (4-HAP) by the Friedel-Crafts acetylation of phenol with acetic acid as the acetylating agent.

Phenol (9.4 g, 0.1 moles) and acetic acid (12.0 g, 0.2 moles) were charged to a 300 ml Hastelloy C autoclave at room temperature. The reactor was evacuated and cooled to −20° C. HF (100 g, 5 moles) was then transferred into the reactor. The reactor was heated to 80° C. and maintained for 1 hour at reaction temperature. At the end of the reaction the reactor was cooled to 20° C. and the excess HF was vented to a KOH scrubber. Ethyl acetate was added to the contents of the reactor. The mixture was then neutralized with 45% aqueous KOH. The resulting organic phase was separated, dried over MgSO$_4$ and evaporated to afford a yellow solid which contained 13.1 g (0.096 moles) of 4-HAP.

EXAMPLE 5

This example illustrates the formation of 4-hydroxyacetophenone oxime from 4-hydroxyacetophenone and hydroxylamine hydrochloride.

A solution was prepared by adding 13.6 g (0.1 mol) of 4-hydroxyacetophenone, 7.6 g (0.11 mol) of hydroxylamine hydrochloride, and 10 g of water to 40 mL of ethanol. To the solution was added 5.0 g of 30% ammonium hydroxide which was then heated at reflux for 2 h. The ethanol was removed on a rotary evaporator to yield a yellow oil. An extractive work-up afforded 15.1 g (99%) of 4-hydroxyacetophenone oxime.

EXAMPLE 6

This example illustrates the formation of 4-hydroxyacetophenone oxime from 4-hydroxyacetophenone and hydroxylamine sulfate.

A solution was prepared by adding 20.4 g (0.15 mol) of 4-hydroxyacetophenone and 13.0 g (0.08 mol) of hydroxylamine sulfate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 7

This example illustrates the formation of 4-hydroxyacetophenone oxime from 4-hydroxyacetophenone and hydroxylamine phosphate.

A solution was prepared by adding 20.4 g (0.15 mol) of 4-hydroxyacetophenone and 12.9 g (65.6 mmol) of hydroxylamine phosphate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 8

This example illustrates the formation of 4-acetoxyacetanilide (AAA) by the Beckmann rearrangement and accompanying acetylation of 4-hydroxyacetophenone oxime using an acidic ion-exchange resin as catalyst.

A mixture of 3.0 g (22.0 mmol) of 4-hydroxyacetophenone oxime, 3.0 g of Amberlyst 15 (a sulfonic acid ion-exchange resin made by Rohm & Haas), and 75 mL of a mixture of glacial acetic acid and acetic anhydride (1:1) was heated at reflux under nitrogen for 4 h. The ion-exchange resin was then removed and the acetic acid/acetic anhydride was distilled in vacuo to yield yellow-white crystals. The crystals were dissolved in ethyl acetate and treated with activated carbon and anhydrous magnesium sulfate. The mixture was filtered and the solvent was removed on a rotary evaporator to yield 3.4 g (80.4%) of yellow crystals of 4-acetoxyacetanilide (AAA).

EXAMPLE 9

This example illustrates the formation of 4-acetoxyacetanilide (AAA) by the Beckmann rearrangement and accompanying acetylation of 4-hydroxyacetophenone oxime using methanesulfonic acid as catalyst.

A solution of 10 g (66.2 mmol) of 4-hydroxyacetophenone oxime, 1.6 of 70% methanesulfonic acid, 50 g of acetic anhydride and 100 g of glacial acetic acid was heated at reflux under nitrogen for 2 h. Rotary evaporation of the solution yielded 17.0 of light brown crystals. Recrystallization from water yielded 6.7 g (52.4%) of 4-acetoxyacetanilide (AAA). The mother liquor contained 32.0% of AAA for a total yield of 84.4%.

EXAMPLE 10

This example illustrates the formation of 4-acetoxyacetanilide (AAA) by the Beckmann rearrangement and accompanying acetylation of 4-hydroxyacetophenone oxime using phosphoric acid ($H_3PO_4$) as catalyst.

To a mixture of 100 g of glacial acetic acid, 50 g of acetic anhydride, and 3.6 g of 85% $H_3PO_4$, sparged with nitrogen for 30 minutes, was added 10 g of 4-hydroxyacetophenone oxime. The mixture was heated at reflux for 1 hour under a nitrogen atmosphere, then cooled to room temperature and neutralized with 13% $Na_2CO_3$. The mixture was evaporated to dryness using a rotary evaporator and the solid was dissolved in 200 g of boiling water. After hot filtration, the solution was allowed to cool and stand overnight. The ensuing white crystals were collected, washed with 20 mL of water, and dried in a vacuum oven (60° C./100 mm Hg) for 2 hours. Upon drying, 9.4 g (73.9%) of white crystalline plates of 4-acetoxyacetanilide having a melting point of 148°–150° C. was obtained. An additional 0.8 g of AAA and 1.5 g of N-acetyl-para-aminophenol (APAP) were reclaimed from the mother liquor.

The procedures of the examples may also be used to prepare N-acetyl-(4-acetoxy-3-methylphenyl) amine from o-cresyl acetate or o-cresol and acetic acid, and acetic anhydride; N-propionyl-(4-propionoxyphenyl) amine from phenyl propionate or phenol and propionic acid, and propionic anhydride; and N-n-butyryl-(4-n-butyroxyphenyl) amine from phenyl n-butyrate or phenol and n-butyric acid, and n-butyric anhydride, in the first and second reactions respectively.

The N-acyl-acyloxy aromatic amines, e.g. AAA, of this invention may be utilized as monomers in the preparation of poly(ester-amide)s capable of forming an anisotropic melt phase and suitable for being formed into shaped articles such as molded articles, fibers and films, as shown, for example in U.S. Pat. Nos. 4,330,457; 4,339,375; 4,341,688; 4,351,918; and 4,355,132.

The N-acyl-acyloxy aromatic amines of this invention, e.g. AAA, may also be hydrolyzed to form the corresponding N-acyl-hydroxy aromatic amine, e.g. N-acetyl-para-aminophenol (APAP) which is one of the most widely used over-the-counter analgesics. The following example illustrates this process:

EXAMPLE 11

A mixture of 5 g (25.9 mmol) of 4-acetoxyacetanilide (AAA), 1.4 g of 70% methanesulfonic acid, and 50 g of water was heated at reflux for 1 hr. Upon cooling, white crystals formed. Analysis (GLC) of the crystals as well as the aqueous solution indicated 90% conversion of the AAA to N-acetyl-para-aminophenol (APAP).

We claim:

1. A process comprising contacting a hydroxy aromatic ketone, wherein aromatic is a divalent aromatic radical resulting from the removal of two ring hydrogen atoms from benzene, naphthalene, or biphenyl, said divalent aromatic radical being unsubstituted are substituted with radicals of the group consisting of $C_1$–$C_8$ alkyl, alkenyl, alkynyl, halogen, hydroxy, amino, and sulfhydryl, with hydroxylamine or a hydroxylamine salt and a base to form the ketoxime of said ketone, and contacting said ketoxime with a carboxylic acid anhydride and a Beckmann rearrangement catalyst to form an N-acyl-acyloxy aromatic amine.

2. The process of claim 1 wherein said hydroxy aromatic ketone is 4-hydroxyacetophenone, said ketoxime is 4-hydroxyacetophenone oxime, said anhydride is acetic anhydride, and said N-acyl-acyloxy aromatic amine is 4-acetoxyacetanilide.

3. The process of claim 2 wherein said 4-acetoxyacetanilide is hydrolyzed to form N-acetyl-para-aminophenol.

4. A process comprising contacting an ester of a phenolic compound and a carboxylic acid, with a Fries rearrangement catalyst to form a hydroxy aromatic ketone, wherein aromatic is a divalent aromatic radical resulting from the removal of two ring hydrogen atoms from benzene, naphthalene, or biphenyl, said divalent aromatic radical being unsubstituted or substituted with radicals of the group consisting of $C_1$–$C_8$ alkyl, alkenyl, alkynyl, halogen, hydroxy, amino, and sulfhydryl, contacting said ketone with a hydroxylamine salt and a base to form a ketoxime of said ketone, and contacting said ketoxime with a carboxylic acid anhydride and a Beckman rearrangement catalyst to form an N-acyl-acyloxy aromatic amine.

5. The process comprising contacting a phenolic compound and an acylating agent with a Friedel-Crafts catalyst to form a hydroxy aromatic ketone, wherein aromatic is a divalent aromatic radical resulting from the removal of two ring hydrogen atoms from benzene, naphthalene, or biphenyl, said divalent aromatic radical being unsubstituted or substituted with radicals of the group consisting of $C_1$–$C_8$ alkyl, alkenyl, alkynyl, halogen, hydroxy, amino, and sulfhydryl, contacting said ketone with a hydroxylamine salt and a base to form a ketoxime of said ketone, and contacting said ketoxime with a carboxylic acid anhydride and a Beckman rearrangement catalyst to form an N-acyl-acyloxy aromatic amine.

6. The process of claim 4 wherein said Fries rearrangement catalyst is hydrogen fluoride.

7. The process of claim 5 wherein said Friedel-Crafts catalyst is hydrogen fluoride.

* * * * *